US009428835B2

(12) United States Patent
Machida et al.

(10) Patent No.: US 9,428,835 B2
(45) Date of Patent: Aug. 30, 2016

(54) COBALT BASE FILM-FORMING METHOD, COBALT BASE FILM-FORMING MATERIAL, AND NOVEL COMPOUND

(71) Applicants: GAS-PHASE GROWTH LTD., Koganei-shi (JP); Tokyo Electron Limited, Minato-Ku (JP)

(72) Inventors: Hideaki Machida, Kunitachi (JP); Masato Ishikawa, Nakano-ku (JP); Hiroshi Sudoh, Koganei (JP); Yumiko Kawano, Nirasaki (JP); Kazutoshi Iwai, Nirasaki (JP)

(73) Assignees: GAS-PHASE GROWTH LTD., Koganei-shi (JP); Tokyo Electron Limited, Minato-ku (JE)

(*) Notice: Subject to any disclaimer, the term of this patent is extended or adjusted under 35 U.S.C. 154(b) by 151 days.

(21) Appl. No.: 14/349,037

(22) PCT Filed: Oct. 4, 2012

(86) PCT No.: PCT/JP2012/075855
§ 371 (c)(1),
(2) Date: Apr. 1, 2014

(87) PCT Pub. No.: WO2013/051670
PCT Pub. Date: Apr. 11, 2013

(65) Prior Publication Data
US 2014/0248427 A1    Sep. 4, 2014

(30) Foreign Application Priority Data
Oct. 7, 2011    (JP) ................ 2011-222562

(51) Int. Cl.
*C23C 16/18*    (2006.01)
*C23C 18/08*    (2006.01)
(Continued)

(52) U.S. Cl.
CPC ............ *C23C 18/08* (2013.01); *C07F 15/065* (2013.01); *C23C 16/18* (2013.01); *C23C 18/04* (2013.01)

(58) Field of Classification Search
CPC ............ C23C 16/18; C23C 16/45523; C23C 16/45527; C23C 16/45557
See application file for complete search history.

(56) References Cited

U.S. PATENT DOCUMENTS

2006/0141155 A1    6/2006   Gordon et al.
2007/0264816 A1*   11/2007  Lavoie .................... C23C 16/18
                                                        438/618

(Continued)

FOREIGN PATENT DOCUMENTS

JP    2006 511716    4/2006
JP    2006 299407    11/2006

(Continued)

OTHER PUBLICATIONS

Lim et al., "Atomic Layer Deposition of transition metals," 2003, Nature Materials, vol. 2, pp. 749-750.*

(Continued)

*Primary Examiner* — Robert Vetere
(74) *Attorney, Agent, or Firm* — Oblon, McClelland, Maier & Neustadt, L.L.P (57) ABSTRACT

A present invention provide a technique for easily forming a high-quality cobalt base film, which have a small specific resistance. The present invention comprises a transportation process of a Co[i-C3H7NC(C2H5)N-i-C3H7]2, and a film formation process by decomposition of the Co[i-C3H7NC(C2H5)N-i-C3H7]2. The film formation process comprises at least a first film formation process and a second film formation process. In the first film formation process, a film formation chamber is supplied with at least NH3 and/or NH3 product compound, and is not virtually supplied with H2. In the second film formation process, the film formation chamber is supplied with at least NH3 and/or NH3 product compound, and H2. An internal pressure of the film formation chamber in the first film formation process is higher than an internal pressure of the film formation chamber in the second film formation process.

11 Claims, 3 Drawing Sheets

(51) Int. Cl.
*C07F 15/06* (2006.01)
*C23C 18/04* (2006.01)

(56) References Cited

U.S. PATENT DOCUMENTS

2009/0029047 A1 1/2009 Yoshii et al.
2009/0130859 A1 5/2009 Itatani et al.

FOREIGN PATENT DOCUMENTS

| JP | 2011 63848 | 3/2011 |
|---|---|---|
| WO | 2007 058120 | 5/2007 |
| WO | 2011 027834 | 3/2011 |
| WO | 2011 027835 | 3/2011 |
| WO | 2011 040385 | 4/2011 |

OTHER PUBLICATIONS

Li, J. et al., "On the Relative Stability of Cobalt- and Nickel-Based Amidinate Complexes Against β-Migration", International Journal of Quantum Chemistry, vol. 109, No. 4, pp. 756-763, (2009).
Li, Z. et al., "Synthesis and characterization of volatile liquid cobalt amidinates", Dalton Transactions, pp. 2592-2597, (2008).
International Search Report Issued Dec. 25, 2012 in PCT/JP12/075855 Filed Oct. 4, 2012.

* cited by examiner

COBALT BASE FILM-FORMING METHOD, COBALT BASE FILM-FORMING MATERIAL, AND NOVEL COMPOUND

TECHNICAL FIELD

The present invention relates to, for example, a cobalt base film-forming technique.

BACKGROUND ART

There is a demand for a cobalt base film (e.g., a film made of metallic cobalt, a cobalt alloy, a cobalt oxide, and a cobalt nitride) in various fields such as an electrically-conducting material field and a magnetic material field. In recent years, the cobalt alloy, e.g., a Co WP alloy, draws attention as a protective film for protecting copper wiring to be used for an LSI. A cobalt silicide that is obtained by formation of a metal Co film on Si and the subsequent heating thereof draws attention as a contact material.

In forming a cobalt base film by a chemical vapor deposition or an atomic layer control growth method, proposed examples of a source material include a cobalt carbonyl compound, a β-diketonate cobalt complex, and a cyclopentadienyl system cobalt complex.

In a case where the cobalt carbonyl compound or the β-diketonate cobalt complex, each having O (i.e., an oxygen atom) as a film-forming source material compound, are used, resulting films entrap O therein. Therefore, there is no serious problem when the cobalt film is an oxide film. To the contrary, if a target cobalt film is a metal film (including a metal alloy), there comes a problem. Also, if a target cobalt film is a nitride film, there may be a problem. Further, the cobalt carbonyl compound is a compound with CO. Therefore, in synthesizing or forming a film, it is necessary to take a measurement against toxic CO. In other words, there is a danger and a bad handling ability.

Since the cyclopentadienyl system cobalt complex does not have O (i.e., an oxygen atom), basically, the resulting film does not entrap O therein. The cyclopentadienyl system cobalt complex requires a high temperature during film formation. Therefore, the cyclopentadienyl system cobalt complex is not suitable for LSI manufacturing. Further, the cyclopentadienyl system cobalt complex has a high decomposition temperature. That means that the resulting film often entraps C therein.

In the light of the above, these days, a cobalt amidinate complex is proposed as an exemplary material for forming a Co base metal (alloy) film.

For example, a Non Patent Literature 1 (Zhengwen Li, Don Kuen Lee, Michael Coulter, Leonard N. J. Rodriguez and Roy G. Gordon, Dalton Trans., 2008, 2592-2597) and a Patent Literature 1 (JP P2006-511716 A) (WO2004/046417)) propose a compound expressed by the following general formula.

In the above general formula, $R_1$, $R_2$, $R_3$, $R_4$, $R_5$, and $R_6$ are selected from any one of hydrogen, an alkyl group, an aryl group, an alkenyl group, an alkynyl group, a trialkylsilyl group, a fluoro-alkyl group, or another non metal atoms or group. For example, the $R_1$, $R_2$, $R_3$, $R_4$, $R_5$, and $R_6$ are selected from the alkyl group or the fluoro-alkyl group, or the silyl alkyl group having 1 to 4 carbon atoms.

The Non Patent Literature 1 proposes bis(N,N'-diisopropylacetamidinate)cobalt (e.g., in the above general formula, $R_1=R_4=CH_3$, $R_2=R_3=R_5=R_6=C_3H_7$).

Compounds discussed as examples in the Patent Literature 1 are bis(N,N'-diisopropylacetamidinate)cobalt (e.g., in the above general formula, $R_1=R_4=CH_3$, $R_2=R_3=R_5=R_6=C_3H_7$), bis(N,N'-di-tert-butylacetamidinate)cobalt (e.g., in the above general formula, $R_1=R_4=CH_3$, $R_2=R_3=R_5=R_6=C_4H_9$), and bis(N,N'-disecbutylacetamidinate)cobalt (e.g., in the above general formula, $R_1=R_4=CH_3$, $R_2=R_3=R_5=R_6=C_4H_9$).

The compound (i.e., the bis(N,N'-diisopropylacetamidinate)cobalt) is made of N,N'-diisopropylcarbodiimide currently used as a standard source material in a peptide synthesis field. Therefore, the compound is synthesized conveniently at low cost. Further, under high vacuum (e.g., 0.05 ton), the compound can be volatilized at a temperature of about 80° C.

The compound, however, has a melting point at 84° C. (see, Non Patent Literature 1). Therefore, if there is a cold spot in piping, solidification/blocking-up may occur during transportation of the compound. Therefore, there is a rigorous demand with respect to a temperature management of film formation equipment, which results in a reduced mass-productiveness. Further, since the compound has a solid body at room temperature, it is difficult to mass-produce the compound having high purity as a film forming material in the LSI.

A Patent Literature 2 (JP P2011-63848 A) also proposes the compound expressed by the above general formula. More specifically, the Patent Literature 2 proposes a compound expressed by the following formula (i.e., expressed in the above general formula, $R_1=R_4=CH_3$, $R_2=R_5=C_4H_9$, $R_3=R_6=C_2H_5$: Co(tBu-Et-Et-amd)$_2$).

The compound having the above formula proposed by the Patent Literature 2 has not so much problem as the problem held by the bis(N,N'-diisopropylacetamidinate)cobalt.

Whereas, a boiling point of the compound is, though it is liquid, high under high vacuum. This makes the compound difficult to volatilize. During formation of a film, an amount of source material capable of being supplied to a film forming space gets low. As a result, the optimum step coverage may not be obtained. Further, the compound has a left-right asymmetry structure. This makes it difficult to synthesize the compound and makes it expensive in manufacturing thereof.

CITATION LIST

[Non Patent Literature]
[Non Patent Literature 1]
Zhengwen Li, Don Kuen Lee, Michael Coulter, Leonard N. J. Rodriguez and Roy G. Gordon, Dalton Trans., 2008, 2592-2597
[Patent Literature]
[Patent Literature 1]
JP P2006-511716 A (WO2004/046417)
[Patent Literature 2]
JP P2011-63848 A

SUMMARY OF INVENTION

Technical Problem

The present invention was made in order to solve the above described problem. Specifically, an object of the present invention is to provide a technique for easily forming a high-quality cobalt base film, which is unlikely to induce a solidification/blocking-up midway in piping, can be stably supplied by a satisfactory amount in creating a reaction limited state, and is excellent in coatablility. Another object of the present invention is to obtain a source material having a low melting point and being liquid at about 40° C. Further another object of the present invention is to obtain the above source material for forming a film to be used herein at low cost.

Solution to Problem

Extensive research and study for solving the above described problem has been made.

As a result, it was found that bis(N,N'-diisopropyl-propionamidinate)cobalt (i.e., Co[i-$C_3H_7$NC($C_2H_5$)N-i-$C_3H_7$]$_2$) had a melting point of about 38° C. (at the highest equal to or less than about 40° C.).

The compound is liquefied even when it is slightly wormed from the room temperature. This allows easy gasification of the compound. Further, it is possible to eliminate or reduce occurrence of solidification/blocking-up at a cold spot midway in piping on the way to a film formation chamber (i.e., a decomposition chamber or a reaction chamber).

In the light of the above, it was also found that a formation of a high quality cobalt film (e.g., a cobalt alloy film) was possible according to a chemical vapor deposition or an atomic layer control growth method.

Further, it was also found that the compound could be synthesized at low cost by using, for example, N,N'-diisopropylcarbodimide as a source material. Still further, it was also found that a highly purified compound could be obtained.

The present invention was made based on the above described knowledge.

The above described problem can be solved by a novel compound including
bis(N,N'-diisopropyl-propionamidinate)cobalt.
The above described problem can be solved by a cobalt base film-forming material including
the bis(N,N'-diisopropyl-propionamidinate)cobalt.
The above described problem can be solved by a cobalt base film-forming material including
the bis(N,N'-diisopropyl-propionamidinate)cobalt, and a solvent.

In the present invention, the solvent is at least a kind selected, preferably, from a group consisting of hydrocarbon compounds. Alternatively, the solvent is at least a kind selected from a group consisting of ether system compounds. Further alternatively, the solvent is N,N'-diisopropyl-propionamidine.

The above described problem can be solved by a cobalt base film-forming method including
transporting the cobalt base film-forming material to a film formation chamber, and
forming a cobalt base film on a substrate by decomposition of bis(N,N'-diisopropyl-propionamidinate)cobalt transported to the film formation chamber.

Preferably, the present invention includes supplying $NH_3$ and/or $NH_3$ product compound and $H_2$ to the film formation chamber. (The $H_2$)/(the $NH_3$ and/or $NH_3$ product compound) is, preferably, 0.0001 to 2 (molar ratio). It is preferable that both of the $NH_3$ and/or the $NH_3$ product compound and the $H_2$ are supplied to the film formation chamber. It is also possible either one of the $NH_3$ and/or the $NH_3$ product compound and the $H_2$ is supplied to the film formation chamber depending on conditions.

In the present invention, the film formation process preferably includes at least a first film formation process and a second film formation process. The second film formation process is performed after the first film formation process. Preferably, $P_1$ (i.e., an internal pressure of the film formation chamber during the first film formation process) is higher than $P_2$ (i.e., an internal pressure of the film formation chamber during the second film formation process). Depending on circumstances, it is possible that $P_1$ is set to a value equal to $P_2$. In the second film formation process, preferably, $NH_3$ (and/or $NH_3$ product compound) and $H_2$ are supplied. (The $H_2$)/(the $NH_3$ and/or $NH_3$ product compound) is, preferably, 0.0001 to 2 (molar ratio). Also, in the first film formation process, preferably, $NH_3$ and/or $NH_3$ product compound are supplied. Preferably, $H_2$ is not virtually supplied.

Advantageous Effects of Invention

According to the present invention, a cobalt base film can be formed suitably.

More specifically, the bis(N,N'-diisopropyl-propionamidinate)cobalt as the source material for forming a cobalt base film has a melting point of about 38° C. (at the highest equal to or less than about 40° C.). Therefore, the bis(N,N'-diisopropyl-propionamidinate)cobalt is liquefied by being slightly heated from a room temperature. Thus, the bis(N,N'-diisopropyl-propionamidinate)cobalt is apt to be gasified. That is, the solidification/blocking-up midway in piping on the way to the film formation chamber hardly occurs. In the light of the above, a stable formation of a high quality cobalt film (e.g., a cobalt metal (alloy) film) could be achieved by a chemical vapor deposition or an atomic layer control growth method.

Employment of N,N'-diisopropylcarbodimide as the source material assured obtainment of the bis(N,N'-diisopropyl-propionamidinate)cobalt with high purity at low cost.

DESCRIPTION OF EMBODIMENTS

A first invention is directed to a novel compound. The compound is bis(N,N'-diisopropyl-propionamidinate)cobalt (Co[i-$C_3H_7$NC($C_2H_5$)N-i-$C_3H_7$]$_2$). In the general formula, the compound is a compound of $R_1=R_4$, $R_2=R_3=R_5=R_6=$i-$C_3H_7$.

A second invention is directed to a cobalt base film-forming material. Specifically, the second invention is a material for forming a cobalt base film (e.g., a cobalt metal (alloy) film) by, for example, the chemical vapor deposition or the atomic layer control growth method. The material contains the bis(N,N'-diisopropyl-propionamidinate)cobalt. Preferably, the material further contains a solvent. Preferably, the solvent is at least a kind selected from a group consisting of hydrocarbon system compounds (of any type such as a straight chain type, a branched chain type, and a cyclic type). Alternatively, the solvent is at least a kind selected from a group consisting of ethers. Further alternatively, the solvent is the N,N'-diisopropyl-propionamidine. Preferably, the hydrocarbon system compound is a hydrocarbon system compound having 5 to 40 carbon atoms. Further preferably, the hydrocarbon system compound is a hydrocarbon system compound having 5 to 21 carbon atoms. Examples thereof include pentane ($C_5H_{12}$), hexane ($C_6H_{14}$), heptane ($C_7H_{16}$), octane ($C_8H_{18}$), nonane ($C_9H_{20}$), decane ($C_{10}H_{22}$), undecane ($C_{11}H_{24}$), dodecane ($C_{12}H_{26}$), tridecane ($C_{13}H_{28}$), tetradecane ($C_{14}H_{30}$), pentadecane ($C_{15}H_{32}$), hexadecane ($C_{16}H_{34}$), heptadecane ($C_{17}H_{36}$), octadecane ($C_{18}H_{38}$), nonadecane ($C_{19}H_{40}$), icosane ($C_{20}H_{42}$), and hennicosane ($C_{21}H_{44}$). Among them, the hydrocarbon having 5 to 15 carbon atoms is more preferred. The ether having 4 to 14 carbon atoms is also preferred. Examples of the preferred ether include diethyl ether, tetrahydrofuran, dibutyl ether, dioxane, tetraethylene glycol dimethyl ether, and dibenzyl ether. Meanwhile, among the above exemplified solvents, a hydrocarbon base solvent (having constituent elements of C and H) is more preferable for its high decomposition temperature and stable property. Further, it is inexpensive. For example, an ether base solvent has high solubility but thus may be decomposed at a film formation temperature. Therefore, there is a concern of contamination of oxygen in a film.

A third invention is directed to a cobalt base film-forming method, more specifically, to a method for forming a cobalt base film (e.g., a cobalt metal (alloy) film) by, for example, a chemical vapor deposition or an atomic layer control growth method. As a matter of course, the film is not limited to the metal film. For example, the film may be a silicide film. Alternatively, the film may be a nitride film. The present method includes a transporting process for transporting the cobalt base film-forming material to a film formation chamber. The present method includes a film formation process for forming a cobalt base film on a substrate by decomposition of bis(N,N'-diisopropyl-propionamidinate)cobalt transported to the film formation chamber. In forming the cobalt base film, the film may be formed in one step or may be formed in two or more steps. In forming the cobalt base film in one step, there is one film formation condition throughout the film formation process. In forming the cobalt base film in two or more steps, there are two or more film formation conditions throughout the film formation process. For example, in forming the cobalt base film in two or more steps, after a film is formed under a condition A, another film is formed under a condition B($\neq$A).

In forming the cobalt base film in one step, preferably, $NH_3$ and/or $NH_3$ product compound and $H_2$ are supplied to the film formation chamber. (The $H_2$)/(the $NH_3$ and/or $NH_3$ product compound) is preferably 0.0001 to 2. The value is a molar ratio. If the $NH_3$ product compound is employed, the value of the molar ratio is a value by $NH_3$ thus generated. In the present film formation process, it is preferable that both of the $H_2$ and the $NH_3$ (and/or the $NH_3$ product compound) are employed. It is noted that $H_2$ may not be supplied in the present film formation process. If a supply of $H_2$ is 0, the value (i.e., the molar ratio) is 0.

In forming the cobalt base film in more than two steps, such formation process preferably includes at least a first film formation process and a second film formation process. The second film formation process follows the first film formation process. Preferably, $P_1$ (i.e., an internal pressure of the film formation chamber in the first film formation process) is higher than $P_2$ (i.e., an internal pressure of the film formation chamber in the second film formation process). Depending on the situation, it is possible to make a value of the $P_1$ equal to a value of $P_2$. In the second film formation process, preferably, both of the $NH_3$ (and/or the $NH_3$ product compound) and the $H_2$ are supplied. Preferably, (the $H_2$)/(the $NH_3$ and/or $NH_3$ product compound) is 0.0001 to 2. The value is a molar ratio. In a case where the $NH_3$ product compound is employed, the value of the molar ratio is a value by $NH_3$ thus generated. Preferably, in the first film formation process, $NH_3$ (and/or $NH_3$ product compound) is supplied. It is noted that, preferably, $H_2$ is not virtually supplied.

In the Co base film obtained in a manner as described above, O component and C component as impurities in the resulting film were very small in amount. Therefore, the impurities such as O and C could not be detected by an XPS (i.e., an X-RAY PHOTOELECTRON SPECTROSCOPY). In other words, the resulting film was of high purity.

Further, a trouble hardly occurred in the film deposition process. For example, a source material of 200 g was subjected to gasification to form a film and, after consuming 170 g of the source material, a source material vessel was removed to observe an inside of the piping. No solidification/blocking-up was observed midway in the piping on the way to the film formation chamber.

Hereinafter, the present invention will be described in detail with reference to specific examples. It is to be noted that the present invention is not limited to the following examples.

[Synthetic Method I of bis(N,N'-diisopropyl-propionamidinate)cobalt]

A reaction was performed under inert gas atmosphere. N,N'-diisopropylcarbodimide (63.1 g) was dissolved in diethyl ether (1000 ml). The resulting solution was chilled to −40° C. A benzene solution containing ethyllithium (0.5 mol) was gradually dropped into the solution, followed by four hour stirring at room temperature. This reaction mixture was gradually dropped into a solution in which cobalt chloride (33 g) was suspended in tetrahydrofuran (600 ml), followed by four hour-stirring. After the solvent was distilled, normal hexane (1500 ml) was added thereto. Then, the insoluble matters were filtered out therefrom. After the solvent was distilled, reduced-pressure (0.1 torr) distillation was performed.

As a result, bis(N,N'-diisopropyl-propionamidinate)cobalt was obtained.

A yield was 80 g (80%). A boiling point was 83° C. A melting point was 37° C.

[Synthetic Method II of bis(N,N'-diisopropyl-propionamidinate)cobalt]

A reaction was performed under inert gas atmosphere. N,N'-diisopropylcarbodimide (49.5 g) was dissolved in diethyl ether (200 ml). The resulting solution was chilled to 0° C. An ether solution containing ethylmagnesium bromide (0.43 mol) (controlled by magnesium and bromic ether) was gradually dropped into the solution, followed by four hour-stirring at room temperature. The reaction mixture was deactivated by water. The deactivated reaction mixture was controlled by aqueous sodium hydroxide so as to have a pH equal to or more than 12. After the pH control, the ether layer was separated. A water layer was extracted by using chloroform to be bonded to the ether layer. Then, the solvent was distilled. After the solvent was distilled, reduced-pressure distillation was performed.

Thus, N,N'-diisopropyl-propionamidine was obtained.

A yield was 50.3 g (82%).

A measurement result by $^1$H-NMR was as described below. The compound was identified from a chemical shift position, a shortage of peak, and an area.

$^1$H-NMR ($C_6D_6$, ppm): 0.84 (t, 3H, $CH_2CH_3$), 1.14 (m, 12H, $CH(CH_3)_2$), 1.74 (q, 2H, $CH_2CH_3$), 3.8 (br, 2H, $CH(CH_3)_2$)

The N,N'-diisopropyl-propionamidine (50 g, 0.32 mol) was added to diethyl ether (800 ml), followed by being chilled to −40° C. A hexane solution containing normal butyl lithium (0.32 mol) was gradually dropped into the solution, followed by four hour-stirring at room temperature. This reaction mixture was gradually dropped into a solution in which a cobalt chloride (20.7 g, 0.16 mol) was suspended to tytrahydrofuran (600 ml), followed by four hour-stirring. After the solvent was distilled, normal hexane (1200 ml) was added thereto. Then, insoluble matters were filtered out therefrom. After the solvent was distilled, reduced-pressure (0.1 torr) distillation was performed.

Bis(N,N'-diisopropyl-propionamidinate)cobalt was obtained in this manner.

A yield was 56 g (93%). A boiling point was 83° C. A melting point was 37° C.

[Synthetic Method of bis(N,N'-diisopropylacetamidinate)cobalt]

A reaction was performed under inert gas atmosphere. N,N'-diisopropylcarbodimide (124 g) was dissolved in the ditheyl ether (700 ml). This solution was chilled to −40° C. An ether solution containing methyl lithium (0.98 mol) was gradually dropped into the solution, followed by four hour-stirring at room temperature. This reaction mixture was gradually dropped into a solution in which a cobalt chloride (64 g) was suspended in tetrahydrofuran (500 ml), followed by four hour-stirring. After the solvent was distilled, normal hexane (1500 ml) was added thereto. Subsequently, insoluble matters were filtered out therefrom. After the solvent was distilled, sublimation was performed under reduced-pressure (0.1 ton).

Bis(N,N'-diisopropylacetamidinate)cobalt was obtained in this manner.

However, it was hard to remove thus obtained bis(N,N'-diisopropylacetamidinate)cobalt from a sublimation apparatus. Therefore, a rough yield was 110 g (64%). Because of sublimation and purification, it was not possible to perform continuous purification. For example, clogging occurred in the apparatus many times during the sublimation and purification. To solve this problem, purification and extraction was performed in several times. It was impossible to perform high quality purification. A melting point was 84° C. (See, Non Patent Literature).

[Formation of Co Thin Film]

Example 1

Figure 1:
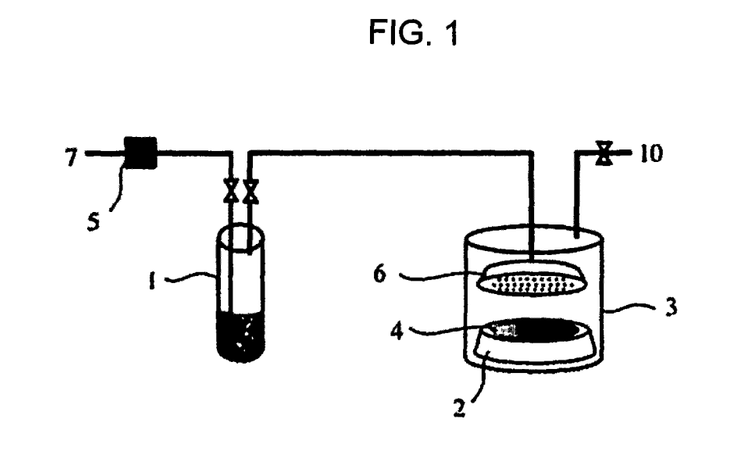
FIG. 1 is a schematic view of a CVD system.

FIG. 1 is a schematic view of an apparatus for forming a Co base film. In FIG. 1, 1 denotes a source material vessel, 2 denotes a substrate heater which holds and heats a substrate, 3 denotes a film formation chamber (i.e., a decomposition reaction furnace), 4 denotes a substrate, 5 denotes a flow rate controller, and 6 denotes a shower head. 7 denotes carrier gas (e.g., hydrogen or inert gas such as Ar and $N_2$). 10 denotes additive gas (e.g., inert gas such as Ar and $N_2$ and reducing gas such as $H_2$ and $NH_3$) to be introduced into the film formation chamber during the film formation process.

With the apparatus of FIG. 1, a Co film was formed on the substrate 4.

Specifically, bis(N,N'-diisopropyl-propionamidinate)cobalt was introduced into the source material vessel 1. A source material was heated by a heater (not shown) disposed on the source material vessel 1 to 90° C. Hydrogen gas (i.e., carrier gas) was supplied at a rate of 20 ml/min. for bubbling. This introduces the bis(N,N'-diisopropyl-propionamidinate)cobalt into the film formation chamber 3 in association with the hydrogen gas. A wall of the film formation chamber 3, the shower head 6, and piping from the source material vessel 1 to the shower head 6 were heated to 120° C. The film formation chamber 3 was evacuated by a pump (not shown). A pressure regulating valve (not shown) between the film formation chamber 3 and the pump controls the chamber 3 to a desired film formation pressure 1 kPa. The substrate 4 was heated to 280° C. by the substrate heater 2. As a result, a film was formed on the substrate 4.

The film formed in the above described manner was excellent in in-plane uniformity. This film was checked by the XPS. As a result, it is confirmed that a rate of C, O, and N in the film was equal to or less than 5 at. %.

Example 2

A device of FIG. 1 was employed to form a Co film on the substrate 4. A film formation was performed in a manner similar to Example 1 except for using Ar gas (10 sccm) as the carrier gas 7 and, Ar gas (40 sccm), $NH_3$ gas (20 sccm), and $H_2$ gas (80 sccm) as the additive gas 10 to be added during the film formation. It took 30 minutes for forming a film.

As a result, a Co film having a thickness of 37 nm and a specific resistance of 38 µΩ·cm was formed on the substrate 4. As a result of a chemical composition analysis by the XPS, a rate of C, O, and N in the film was equal to or less than 5 at. %.

Example 3

A device of FIG. 1 was employed to form a Co film on the substrate 4. A film formation was performed in a manner similar to Example 1 except for using Ar gas (25 sccm) as the carrier gas 7, and Ar gas (100 sccm), $NH_3$ gas (500 sccm), and $H_2$ gas (50 sccm) as the additive gas 10 during the film formation. It took 20 minutes to form a film.

As a result, a Co film having a thickness of 23.6 nm, a sheet resistance of 18.8Ω/□, and a specific resistance of 44.4

μΩ·cm was formed on the substrate 4. As a result of a chemical composition analysis by the XPS, a rate of C, O, and N in the film was equal to or less than 5 at. %.

Example 4

Figure 2:
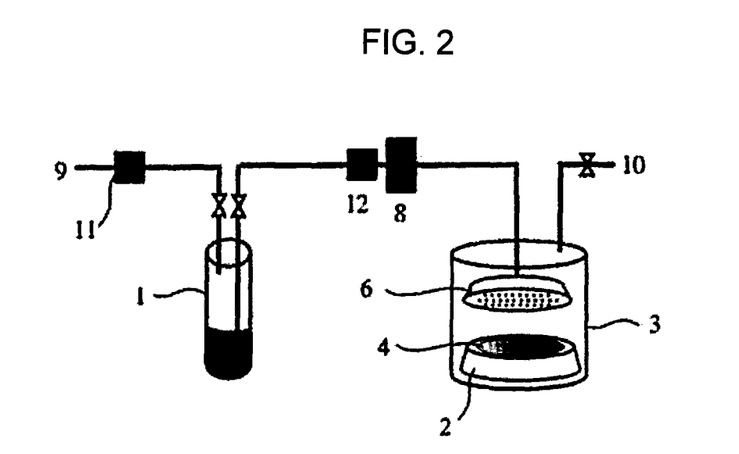
FIG. 2 is a schematic view of another CVD system.

FIG. 2 is a schematic view of a device for forming a Co base film. In FIG. 2, 1 denotes the material vessel, 2 denotes the substrate heater, 3 denotes the film formation chamber, 4 denotes the substrate, 6 denotes the shower head, and 8 denotes a vaporizer. 9 is material pressure feed gas (e.g., inert gas such as He and Ar) that forcibly feeds a material from the material vessel 1 to the vaporizer 8. 10 is the additive gas (e.g., inert gas such as Ar and $N_2$ and reducing gas such as $H_2$ and $NH_3$) to be introduced into the film formation chamber during the film formation process. 11 denotes a pressure controller that controls a pressure of the material pressure feed gas 9. 12 denotes a liquid flow rate controller. The liquid flow rate controller 12 controls a flow rate of a liquid source material to be forcibly fed to the vaporizer 8.

A device of FIG. 2 was employed to form a Co film on the substrate 4.

A decane solution containing bis(N,N'-diisopropyl-propionamidinate)cobalt was introduced into the source material vessel 1. $N_2$ gas was employed as the material pressure feed gas 9, and a pressure thereof was controlled to 0.1 MPa by the material pressure feed gas pressure controller 11. The liquid flow rate controller 12 controlled a flow rate of the decane solution containing the bis(N,N'-diisopropyl-propionamidinate)cobalt to 0.1 mg/min., and thereby the decan solution was forcibly fed. As a result, the decane solution containing the bis(N,N'-diisopropyl-propionamidinate)cobalt was sent to the vaporizer 8. The bis(N,N'-diisopropyl-propionamidinate)cobalt sent to the vaporizer 8 was introduced into the film formation chamber 3 as the carrier gas in association with the Ar gas (50 sccm). As the additive gas 10 to be used during the film formation process, Ar gas (40 sccm), $NH_3$ gas (20 sccm), and $H_2$ gas (80 sccm) were also supplied to the film formation chamber 3. The wall of the film formation chamber 3, the shower head 6, and the piping from the source material vessel 1 to the shower head 6 are heated to 120° C. The film formation chamber 3 was evacuated by using a pump (not shown). The film formation chamber 3 has been controlled to a desired film formation pressure (1 kPa) by a pressure regulating valve (not shown) disposed between the film formation chamber 3 and the pump. The substrate 4 is heated to 300° C. by means of the substrate heater 2. As a result, a film was formed on the substrate 4.

The film formed in the above described manner was excellent in in-plane uniformity. The film was checked by the XPS. The check confirmed that a rate of C, O, and N in the film was equal to or less than 5 at. %.

Example 5

A film was formed on the substrate 4 in a manner similar to Example 4 except for the use of tetrahydrofuran instead of the decane ($C_{10}H_{22}$).

The resulting film was excellent in in-plane uniformity. The film was checked by the XPS. The check confirmed that a rate of C, O, and N in the film was equal to or less than 5 at. %.

Example 6

A film was formed on the substrate 4 in a manner similar to Example 4 except for the use of N,N'-diisopropyl-propionamidine instead of the decane ($C_{10}H_{22}$).

The resulting film was excellent in in-plane uniformity. The film was checked by the XPS. The check confirmed that a rate of C, O, and N in the film was equal to or less than 5 at. %.

Comparative Example 1

A film was formed in a manner similar to Example 1 except for the use of bis(N,N'-diisopropylacetamidinate) cobalt (i.e., a compound disclosed in Non Patent Literature 1 and Patent Literature 1) instead of the bis(N,N'-diisopropyl-propionamidinate)cobalt.

The bis(N,N'-diisopropylacetamidinate)cobalt was introduced into the source material vessel 1. The source material vessel 1 was supplied with hydrogen gas (i.e., carrier gas) of a rate of 20 ml/min. for bubbling. As a result, the bis(N,N'-diisopropylacetamidinate)cobalt was introduced into the decomposition reaction furnace 3 in association with the hydrogen gas. The source material vessel 1 and the piping were heated, respectively, to 90° C. and 120° C. The system was evacuated. The substrate 4 was heated to 280° C.

In cold portions of the source material vessel 1 and the piping, the bis(N,N'-diisopropylacetamidinate)cobalt was solidified to block passages thereof. This made it impossible to continue the work. Next day, a heater was disposed on the piping in order to uniformly heat the piping as much as possible. Then, the work was restarted. However, a flow of the carrier gas (i.e., bubbling) could not be observed, and thus the work was given up.

The source material vessel 1 was opened to be checked. As a result, solidification/blocking-up was found in the bubbling pipe. The source material vessel 1 was subjected to two hour-heating at 100° C. This, however, could not heat throughout the vessel, and the material clogged in the bubbling pipe did not melt. Therefore, the film formation work was given up.

Comparative Example 2

A film was formed in a manner similar to Example 1 except for the use of bis(N-tert-butyl-N'-ethyl-propionamidinate)cobalt instead of the bis(N,N'-diisopropyl-propionamidinate)cobalt.

Specifically, the compound was input into the source material vessel 1. Then, the hydrogen gas (i.e., carrier gas) was supplied to the source material vessel 1 at a rate of 20 ml/min. for bubbling. As a result, the compound was introduced into the film formation chamber 3 in association with the hydrogen gas. The source material vessel 1 and the piping were heated, respectively, to 90° C. and 120° C. The system was evacuated. The substrate 4 was heated to 350° C. As a result, a film was formed on the substrate 4.

The resulting film has, compared with the film obtained in Example 1, less in-plane uniformity and a thinner film thickness. A weight of the source material vessel 1 was measured after the test. The material decreased less than that of the case of Example 1. The reason was assumed that the bis(N-tert-butyl-N'-ethyl-propionamidinate)cobalt has higher boiling point and thus has lower volatility than the bis(N,N'-diisopropyl-propionamidinate)cobalt.

The temperatures of the source material vessel 1 and the piping were elevated, respectively, to 110° C. and 130° C., and the same test was performed. As a result, there was an improvement in the in-plane uniformity but there was only a little increase of the film thickness. The film thickness as obtained from Example 1 could not be obtained.

The substrate 4 was heated to 450° C., and the same test was performed. As a result, finally, a film having an approximately the same thickness as obtained from Example 1 could be obtained. This film was checked by the XPS. It was confirmed that the film contains a large amount of C (carbon) in addition to Co. In other words, the Co film having the purity as obtained in Example 1 could not be obtained here.

Example 7

Bis(N,N'-diisopropyl-propionamidinate)cobalt was introduced into the source material vessel. The source material was heated by a heater disposed on the source material vessel. Carrier gas was supplied for bubbling. This introduces the bis(N,N'-diisopropyl-propionamidinate)cobalt into the film formation chamber. The chamber had an electrical resistance stage heater also serving as a mounting table. A substrate on the mounting table was heated by the heater to 320° C. The chamber was evacuated. In a film formation process, the condition was controlled to the below mentioned pressure and gas flow rate.

[Film Formation Process]
[First Step (Heating Before Formation of Film Under $NH_3/H_2$ Atmosphere)]
Pressure: 8 Torr
Gas flow rate (sccm) ratio: diluted $Ar/NH_3/H_2$=100/200/500
Time: 30 sec.
[Second Step (Formation of Film)]
Pressure: 8 Torr
Gas flow rate (sccm) ratio: diluted $Ar/NH_3/H_2$/carrier Ar=100/200/500/100
Time: 3600 sec.
[Third Step (Heating after Formation of Film Under $NH_3/H_2$ Atmosphere)]
Pressure: 8 Torr
Gas flow rate (sccm) ratio: diluted $Ar/NH_3/H_2$=100/357/236
Time: 600 sec.

The heating before formation of film under the $NH_3$ atmosphere of the first step was performed for the purpose of preliminary keeping a surface of the substrate under atmosphere containing $NH_3$. This facilitated decomposition of a source material compound (i.e., a Co compound) at an early phase of film formation of the second step. The heating after formation of film under $NH_3/H_2$ atmosphere of the third step was performed for the purpose of causing the source material compound (e.g., the Co compound: the Co compound that was before decomposed or insufficiently decomposed) remaining on the surface of the substrate, after completion of the film formation of the second step, to be sufficiently decomposed. Another purpose was to clean the surface of the film.

The carrier Ar serves to carry a material vapor via the source material vessel by a bubbling method. The diluted Ar is to be introduced into a reaction space in the chamber without passing through the source material vessel.

In a lower section of the chamber, in order to avoid an extra film formation on the stage heater at any phase from the first step through the third step, Ar gas called as a bottom purge was caused to distribute therein at a rate of 300 sccm.

During the film formation process, the chamber was controlled at a predetermined pressure while diluted Ar, $NH_3$, $H_2$, carrier Ar, the material vapor, and the bottom purge Ar were distributed therein. For example, the pressure was controlled to, for example, 8 Torr by a pressure regulating valve disposed between the chamber and the vacuum pump.

A Co film was formed on the substrate through the above described steps. The film had a thickness of 65.3 nm. The sheet resistance was 4.093Ω/□. The specific resistance was 26.7 μΩ·cm.

Figure 3:
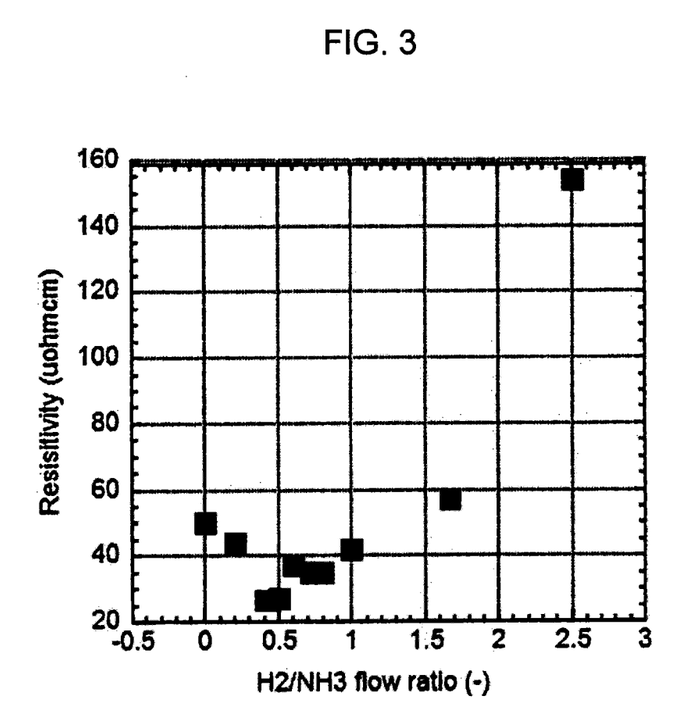
FIG. 3 is a graph illustrating a specific resistance of a Co film.

In the second step (i.e., the film formation process), a film was formed similarly with the flow ratio between $H_2$ and $NH_3$ being changed. A property of the resulting film obtained at the time is illustrated in FIG. 3. FIG. 3 illustrates a relationship between a specific resistance (i.e., a vertical axis) and $-H_2/NH_3$ flow ratio (i.e., a horizontal axis). In FIG. 3, a value when the $H_2/NH_3$ flow ratio is 0 is a specific resistance in a case where the $H_2$ was not supplied. It is known from FIG. 3 that the specific resistance is small when the $H_2/NH_3$ flow ratio (i.e., the molar ratio) is equal to or less than 2, preferably, equal to or less than about 1.5, more preferably, equal to or less than about 1, further preferably, about a range between 0.2 and 0.8, the most preferably, about a range between 0.3 and 0.5.

The film (having the specific resistance of 50.4 μΩ·cm) formed under the condition of $H_2/NH_3$ (flow ratio) was 0 was checked by the XPS. The film (having the specific resistance of 27 μΩ·cm) formed under the condition of $H_2/NH_3$ (flow ratio) was 0.5 was checked by the XPS. As a result, the ratios of C, O, and N in the former film (having the specific resistance of 50.4 μΩ·cm) were, respectively, 1.6 at. %, 2.7 at. %, and 0.7 at. %. The ratios of C, O, and N in the latter film (having the specific resistance of 27 μΩ·cm) were, respectively, 3.8 at. %, 1.0 at. %, and 0.2 at. %. The ratios of C, O, and N in the film were, respectively, a value equal to or less than 5 at. %.

Figure 4:
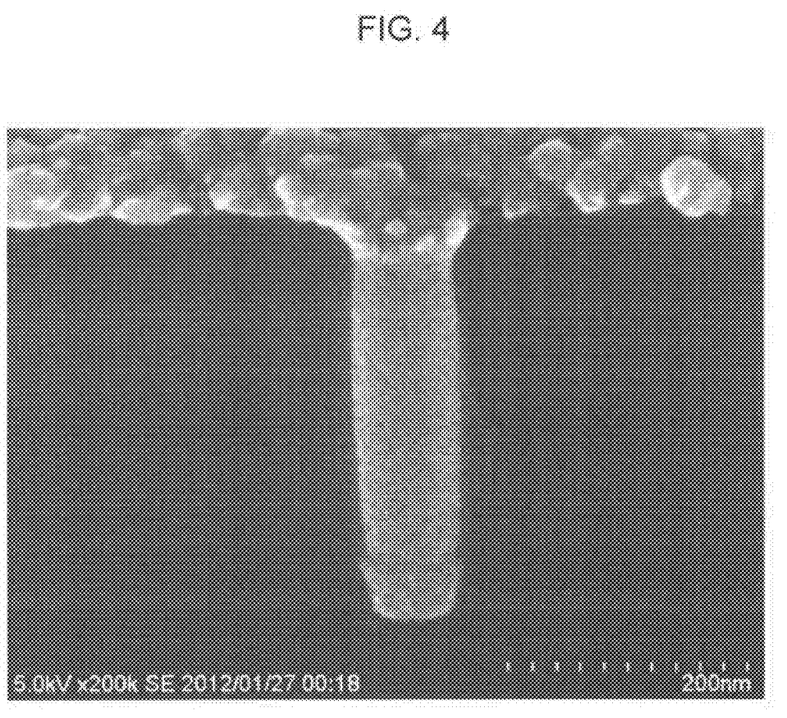
FIG. 4 is a SEM photomicrograph.

FIG. 4 is a SEM photomicrograph upon burying a film into a hole ($H_2/NH_3$ flow rate=1). It is seen from FIG. 4 that the film is suitably buried into a micropore having a diameter of 100 nm and a depth of 300 nm.

Example 8

A film was formed in a manner similar to Example 7 except that the second step (i.e., formation of film) was performed in two steps (including a second step-1 and a second step-2).

[Second Step-1 (First Film Formation Process)]
Pressure: 20 Torr
Gas flow rate (sccm) ratio: diluted $Ar/NH_3/H_2$/Carrier Ar=100/0/500/100
Time: 900 sec.
[Second Step-2 (Step after Second Step-1: Second Film Formation Process)]
Pressure: 8 Torr
Gas flow rate (sccm) ratio: diluted $Ar/NH_3/H_2$/Carrier Ar=100/400/500/100
Time: 900 sec.

By undergoing the above described process, a Co film was formed on the substrate. This film had a thickness of 28.5 nm. A sheet resistance thereof was 6.519Ω/□. A specific resistance was 18.6 μΩ·cm.

A film formation was performed by varying conditions of the two steps. A result thereof is illustrated in the following Tables 1, 2, and 3.

TABLE 1

| ID | Temp (deg C.) | Press (Torr) | time (sec) | diluted Ar (sccm) | H2 (sccm) | NH3 (sccm) | carrier Ar (sccm) |
|---|---|---|---|---|---|---|---|
| Second Step-1 | | | | | | | |
| CoF1-62 | 320 | 8 | 900 | 100 | 0 | 500 | 100 |
| CoF1-61 | 320 | 8 | 900 | 100 | 200 | 200 | 100 |
| Second Step-2 | | | | | | | |
| CoF1-62 | 320 | 8 | 900 | 100 | 200 | 200 | 100 |
| CoF1-61 | 320 | 8 | 900 | 100 | 0 | 500 | 100 |

| ID | Sheet resistance (ohm/sq) | Thickness (nm) | Specific resistance (uohmcm) | Smoothness |
|---|---|---|---|---|
| CoF1-62 | 8.831 | 32.7 | 28.9 | ○ |
| CoF1-61 | 22.6 | 42.5 | 96.1 | X |

TABLE 2

| ID | Temp (deg C.) | Press (Torr) | time (sec) | diluted Ar (sccm) | H2 (sccm) | NH3 (sccm) | carrier Ar (sccm) |
|---|---|---|---|---|---|---|---|
| Second Step-1 | | | | | | | |
| CoF1-62 | 320 | 8 | 900 | 100 | 0 | 500 | 100 |
| CoF1-75 | 320 | 20 | 900 | 100 | 0 | 500 | 100 |
| CoF1-79 | 320 | 20 | 900 | 100 | 0 | 500 | 100 |
| Second Step-2 | | | | | | | |
| CoF1-62 | 320 | 8 | 900 | 100 | 200 | 200 | 100 |
| CoF1-75 | 320 | 8 | 900 | 100 | 200 | 200 | 100 |
| CoF1-79 | 320 | 20 | 900 | 100 | 200 | 200 | 100 |

| ID | Sheet resistance (ohm/sq) | Thickness (nm) | Specific resistance (uohmcm) | Smoothness |
|---|---|---|---|---|
| CoF1-62 | 8.831 | 32.7 | 28.9 | ○ |
| CoF1-75 | 7.027 | 26.6 | 18.7 | ○ |
| CoF1-79 | 13.02 | 17.9 | 23.3 | ○ |

TABLE 3

| ID | Temp (deg C.) | Press (Torr) | time (sec) | diluted Ar (sccm) | H2 (sccm) | NH3 (sccm) | carrier Ar (sccm) |
|---|---|---|---|---|---|---|---|
| Second Step-1 | | | | | | | |
| CoF1-75 | 320 | 20 | 900 | 100 | 0 | 500 | 100 |
| CoF1-76 | 320 | 20 | 900 | 100 | 0 | 500 | 100 |
| CoF1-77 | 320 | 20 | 900 | 100 | 0 | 500 | 100 |
| Second Step-2 | | | | | | | |
| CoF1-75 | 320 | 8 | 900 | 100 | 200 | 200 | 100 |
| CoF1-76 | 320 | 8 | 900 | 100 | 200 | 500 | 100 |
| CoF1-77 | 320 | 8 | 900 | 100 | 400 | 500 | 100 |

| ID | Sheet resistance (ohm/sq) | Thickness (nm) | Specific resistance (uohmcm) | Smoothness |
|---|---|---|---|---|
| CoF1-75 | 7.027 | 26.6 | 18.7 | ○ |
| CoF1-76 | 7.721 | 29.5 | 19.3 | ○ |
| CoF1-77 | 6.591 | 28.5 | 18.6 | ○ |

Table 1 shows the following. In a later phase of the film formation process, when $H_2$ and $NH_3$ were supplied, a film having smaller specific resistance was formed. Also, the resulting film was excellent in smoothness. In an early phase of the film formation process, it was preferable that $H_2$ was not supplied.

Table 2 shows the following. When $P_1$ (i.e., an ambient pressure in an early phase of the film formation process) is higher than $P_2$ (i.e., an ambient pressure in a later phase of the film formation process), a film having smaller specific resistance was obtained. Also, the resulting film was excellent in smoothness.

Table 3 shows the following. When a molar ratio of the $H_2/NH_3$ was 0.4 to 1, a film having a small specific resistance was obtained. Also, the resulting film was excellent in smoothness.

REFERENCE SIGNS LIST 1 source material vessel
2 substrate heater
3 film formation chamber
4 substrate
5 rate controller
6 shower head
7 carrier gas (hydrogen or inert gas such as Ar and $N_2$)
8 vaporizer
9 material pressure feed gas (inert gas such as He and Ar)
10 additive gas upon forming a film (inert gas such as Ar and $N_2$ and reducing gas such as $H_2$ and $NH_3$)
11 material pressure feed gas pressure controller
12 liquid flow rate controller

The invention claimed is:

1. A method for forming a cobalt base film, the method comprising:
   transporting bis(N,N'-diisopropyl-propionamidinate)cobalt to a film formation chamber; and
   forming a cobalt base film on a substrate by decomposition of the bis(N,N'-diisopropyl-propionamidinate)cobalt transported to the film formation chamber;
   wherein:
   the film formation process comprises at least a first film formation process and a second film formation process;
   the second film formation process occurs after the first film formation process;
   an internal pressure of the film formation chamber in the first film formation process is higher than an internal pressure of the film formation chamber in the second film formation process;
   in the first film formation process,
      the film formation chamber is supplied with at least $NH_3$ and/or $NH_3$ product compound, and
      the film formation chamber is not supplied with $H_2$;
   in the second film formation process, the film formation chamber is supplied with at least $NH_3$ and/or $NH_3$ product compound, and $H_2$; and
   ($H_2$)/(the $NH_3$ and/or $NH_3$ product compound) is 0.0001 to 2 (molar ratio).

2. The method for forming a cobalt base film according to claim 1, wherein:
   the bis(N,N'-diisopropyl-propionamidinate)cobalt is added to a solvent; and
   the bis(N,N'-diisopropyl-propionamidinate)cobalt is transported by bubbling.

3. The method for forming a cobalt base film according to claim 2, wherein the solvent is a hydrocarbon compound.

4. The method for forming a cobalt base film according to claim 2, wherein the solvent is an ether compound.

5. The method for forming a cobalt base film according to claim 2, wherein the solvent comprises N,N'-diisopropyl-propionamidine.

6. The method for forming a cobalt base film according to claim 1, wherein the cobalt base film is formed by a chemical vapor deposition.

7. The method for forming a cobalt base film according to claim 1, wherein the cobalt base film is formed by an atomic layer control growth method.

8. The method for forming a cobalt base film according to claim 1, wherein the heating in which the substrate is heated under the $NH_3$ atmosphere occurs after the film formation process.

9. The method for forming a cobalt base film according to claim 1, wherein the heating in which the substrate is heated under $NH_3$ and $H_2$ atmosphere occurs after the film formation process.

10. The method for forming a cobalt base film according to claim 1, wherein the heating in which the substrate is heated under $NH_3$ atmosphere occurs before the first film formation process.

11. The method for forming a cobalt base film according to claim 1, wherein the heating in which the substrate is heated under $NH_3$ and $H_2$ atmosphere occurs before the first film formation process.

* * * * *